United States Patent

Carlsson et al.

[11] 4,076,840
[45] Feb. 28, 1978

[54] SUBSTITUTED CYCLOPROPYL BENZAMIDES AND PHARMACEUTICAL PREPARATIONS AND METHODS OF USE EMPLOYING SUCH COMPOUNDS

[75] Inventors: Per Arvid Emil Carlsson, Goteborg; Per Lennart Lindberg; Borje Vilhelm Wickberg, both of Lund, all of Sweden

[73] Assignee: Astra Lakemedel Aktiebolag, Sodertalje, Sweden

[21] Appl. No.: 689,824

[22] Filed: May 25, 1976

[30] Foreign Application Priority Data

Jun. 9, 1975 Sweden ............................ 7506546

[51] Int. Cl.$^2$ .................. C07C 103/78; A61K 31/165
[52] U.S. Cl. .............................. 424/324; 260/514 H; 260/558 R; 260/561 R; 260/563 R; 260/567.6 M; 424/300; 424/315; 424/319; 424/320; 424/325; 560/115
[58] Field of Search ...................... 260/558 R; 424/324

[56] References Cited

U.S. PATENT DOCUMENTS 3,106,576 10/1963 Kaiser et al. ............... 260/558 R X
3,954,778 5/1976 Teotino et al. ................. 424/324 X

OTHER PUBLICATIONS

Wasserman et al., J. Am. Chem. Soc., 88:22, pp. 5368–5369 (1966).
Roberts et al., CA 46:3506c (1952).

Primary Examiner—Daniel E. Wyman
Assistant Examiner—Thomas A. Waltz
Attorney, Agent, or Firm—Brumbaugh, Graves, Donohue & Raymond

[57] ABSTRACT

Compounds of the formula

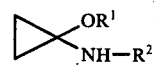

wherein $R^1$ is a hydrogen atom, a methyl group or an ethyl group and $R^2$ is a hydrogen atom,

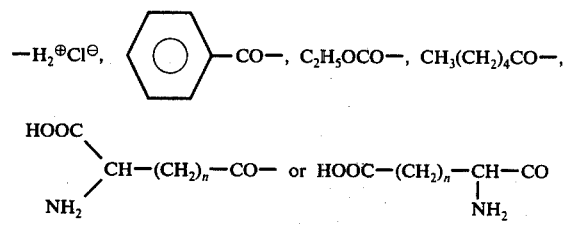

wherein $n$ is 1 or 2, provided that $R^1$ is a methyl or an ethyl group when $R^2$ is a hydrogen atom; methods for the preparation thereof; intermediates useful for their preparation; pharmaceutical preparations containing at least one of these compounds; and the use thereof in the treatment of alcoholism.

12 Claims, No Drawings

SUBSTITUTED CYCLOPROPYL BENZAMIDES AND PHARMACEUTICAL PREPARATIONS AND METHODS OF USE EMPLOYING SUCH COMPOUNDS

This invention relates to new cyclopropanol derivatives, to methods for their preparation and isolation and to new intermediates useful for the preparation of these cyclopropanol derivatives. The invention also relates to the preparation of pharmaceutical preparations containing these cyclopropanol derivatives and to methods for their pharmacological use.

PRIOR ART

In the medical treatment of alcoholism disulfiram

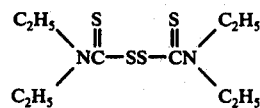

is used widely. However, many side effects can appear in this treatment, some of which are serious. Mental depression, diminished libido and potency, drowsiness, bad breath gastrointestinal disturbances have been reported.

OUTLINE OF THE INVENTION a. General outline

We have found compounds which have durations of the same magnitude as disulfiram but which have fewer side-effects.

More particularly these compounds have the general formula

IA wherein $A^1$ is a hydrogen atom, a hydroxy group, a methoxy group, ethoxy group or an acetoxy group and $A^2$ is a hydroxy group, an amino group, an acetoxy group, a group

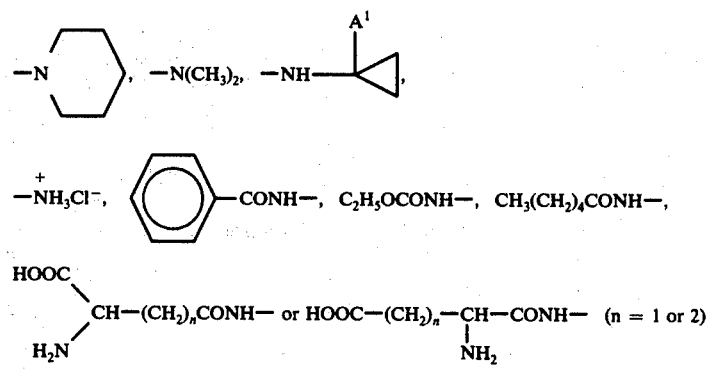

provided that $A^1$ is a hydrogen atom, a methoxy group or an ethoxy group when $A^2$ is an amino group, that $A^2$ is a hydroxy group or an amino group when $A^1$ is a hydrogen atom and that $A^2$ is a hydroxy group or an acetoxy group when $A^1$ is an acetoxy group.

The invention also comprises, where applicable, pharmaceutically acceptable salts of the compounds of the formula I A.

Some of these compounds are described in the literature. Any medical use for these compounds has not however been disclosed in the literature. These structurally known compounds are

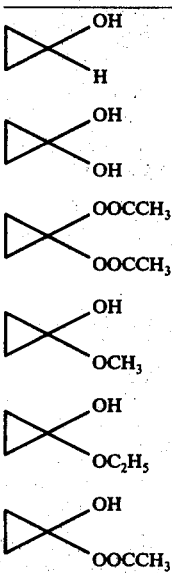

C. H. De Puy et al; J. Org. Chem., 29, 2813 (1964).

W. J. M. van Tilborg; Thesis, Amsterdam 1971.
S. E. Schaafsma; Thesis, Amsterdam 1968.

"

"

"

W. J. M. van Tilborg; Thesis, Amsterdam 1971.

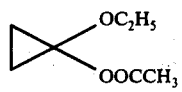 H. H. Wasserman and D. C. Clagett; J. Am. Chem. Soc., 88, 5368 (1966)

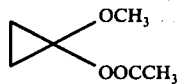 N. J. Turro and W. B. Hammond; Tetrahedron 24, 6017 (1968).

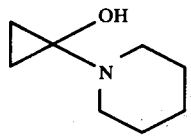 H. H. Wasserman and M. S. Baird; Tetrahedron Lett., 1729 (1970).

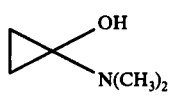 W. J. M. Tilborg; Thesis, Amsterdam 1971.

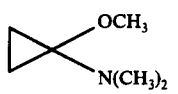 "

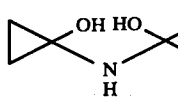 "

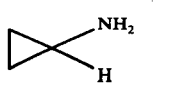 J. D. Roberts and V. C. Chambers; J. Am. Chem. Soc., 73, 3176 (1951).

The compounds of formula I A may be prepared according to methods disclosed in the above mentioned publications or according to methods disclosed in this patent specification (application).

In this application are disclosed for the first time compounds of the general formula

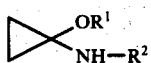   I wherein $R^1$ is a hydrogen atom, a methyl group or an ethyl group and $R^2$ is a hydrogen atom, a group

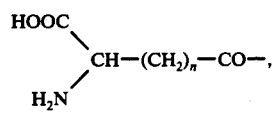

or  HOOC—$(CH_2)_n$—CH—CO—   (n = 1 or 2),
                     |
                     $NH_2$ provided that $R^1$ is a methyl or an ethyl group when $R^2$ is a hydrogen atom.

The invention also comprises pharmaceutically acceptable salts of the compounds of the formula I wherein $R^1$ is a hydrogen atom, a methyl group or an ethyl group and $R^2$ is a hydrogen atom,

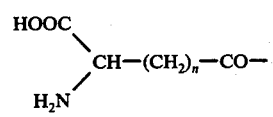

or  HOOC—$(CH_2)_n$—CH—CO—   (n = 1 or 2)
                     |
                     $NH_2$

Where optical isomers of the compounds of this invention are possible, these compounds may be used therapeutically as the racemic mixtures of (+) and (−)-forms, which are obtained by synthesis. They may also be resolved into the corresponding optically pure enantiomers which, likewise, may be used in therapy. The compounds of this invention may be administered in the form of free bases or their salts with non-toxic acids. Some typical examples of these salts are the hydrobromide, hydrochloride, phosphate, sulphate, citrate, tartrate, lactate, acetate and sulphamate.

b. Pharmaceutical preparation

In clinical practice the compounds of the present invention will normally be administered orally, rectally or by injection, in the form of pharmaceutical preparations comprising the active ingredient either as a free base or as a pharmaceutically acceptable nontoxic, acid addition salt, e.g. the hydrochloride, hydrobromide, phosphate, citrate, tartrate, lactate, acetate, sulphate, sulphamate and the like in association with a pharmaceutically acceptable carrier. Accordingly, terms relating to the novel compounds of this invention whether generically or specifically are intended to include both the free amine base and the acid addition salts of the free base, unless the context in which such terms are used, e.g. in the specific examples would be inconsistent with the broad concept. The carrier may be a solid, semisolid or liquid diluent or capsule. These pharmaceutical preparations constitute a further aspect of this invention. Usually the active substance will constitute between 0.1 and 95% by weight of the preparation, more specifically between 0.5 and 20% by weight for preparation intended for injection and between 2 and 50% by weight for preparation suitable for oral administration.

To produce pharmaceutical preparations containing a compound of the invention in the form of dosage units for oral application, the selected compound may be mixed with a solid pulverulent carrier, e.g. lactose, saccharose, sorbitol, mannitol, starches such as potato starch, corn starch or amylopectin, cellulose derivatives, or gelatine, a lubricant such as magnesium stearate, calcium stearate, polyethylene glycol waxes, and the like, and then compressed to form tablets. If coated tablets are required, the cores, prepared as described above, may be coated with a concentrated sugar solution which may contain, e.g. gum arabic, gelatine talcum, titanium dioxide, and the like. Alternatively, the tablet can be coated with a lacquer dissolved in a readily volatile organic solvent or mixture of organic solvents. Dyestuffs may be added to these coatings in order to distinguish readily between tablets containing different active substances or different amounts of the active compound.

For the preparation of soft gelatine capsules (pearl-shaped closed capsules) consisting of gelatine and for example, glycerol or similar closed capsules, the active substance may be admixed with a vegstable oil. Hard gelatine capsules may contain granulates of the active substance in combination with solid, pulverulent carriers such as lactose, saccharose, sorbitol, mannitol, starches (e.g. potato starch, corn starch or amylopectin), cellulose derivatives or gelatine.

Dosage units for rectal application can be prepared in the form of suppositories comprising the active substance in admixture with a neutral fatty base, or gelatine rectal capsules comprising the active substance in admixture with vegetable oil or paraffin oil.

Liquid preparations for oral application may be in the form of syrups or suspensions for example, solutions containing from about 0.2% to about 20% by weight of the active substance herein described, the balance being sugar and a mixture of ethanol, water, glycerol, and propyleneglycol. Optionally such liquid preparations may contain colouring agents, flavouring agents, saccharine and carboxymethylcellulose as a thickening agent.

Solutions for parenteral applications by injection can be prepared in an aqueous solution of a water-soluble pharmaceutically acceptable salt of the active substance preferably in a concentration of from about 0.5% to about 10% by weight. These solutions may also contain stabilizing agents and/or buffering agents and may conveniently be provided in various dosage unit ampoules.

Suitable oral doses of the compounds of the invention are 5–500 mg, preferably 20–150 mg.

c. Preferred embodiment

The preferred compounds of the invention have the formulas

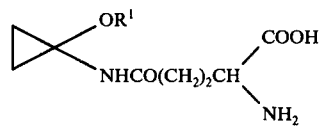

-continued and 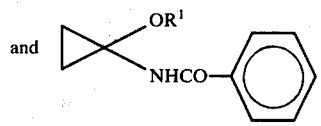

wherein $R^1$ is a hydrogen atom, a methyl or an ethyl group.

d. Methods of preparation

A. The compounds of the formula I wherein $R^1$ is a hydrogen atom, a methyl or an ethyl group and $R^2$ is a hydrogen atom or $-H_2{}^+Cl^-$, provided that $R^1$ is a methyl or an ethyl group when $R^2$ is a hydrogen atom, can be prepared by a. reaction of

with liquid ammonia in a first step and $HCl/H_2O$ in a second step, or b. reaction of

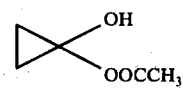

with $NH_3/NH_4Cl$ and $H_2O$ in a first step and HCl in a second step, or c. heating of

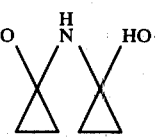

in the presence of $HCl/H_2O$, or d. reaction with hydrochloric acid of a compound of the formula

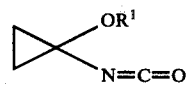

wherein $R^1$ is a methyl or ethyl group, or of a compound of the formula

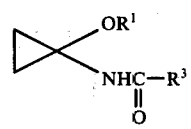

wherein $R^1$ is a hydrogen atom, a methyl group or an ethyl group and $R^3$ is an alkyl group with 1 to 5 carbon atoms or an easily removable alkoxy group such as t-butoxy or benzyloxy, provided that $R^3$ is an alkyl group when $R^1$ is hydrogen, or e. alkaline hydrolysis of a compound of one of the formulas

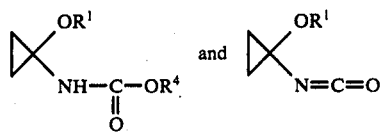 and 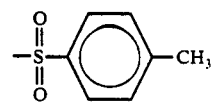

wherein R¹ is a methyl or an ethyl group and R⁴ is an alkyl group with 1 to 5 carbon atoms, and subsequent acidification with hydrochloric acid, or f. reaction of

wherein Z¹ is

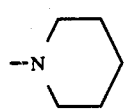

or —N(CH₃)₂, with NH₃/NH₄Cl and H₂O, or g. alkylation of a compound of the formula

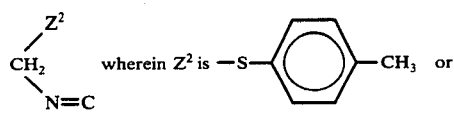 wherein Z² is with 1,2-dibromoethane in the presence of a base such as sodium hydride, to the formation of a compound of the formula

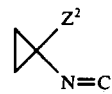

and reaction of this compound with hydrochloric acid.

In reactions a – g compounds of the formula I wherein R¹ is hydrogen and R² is —H₂⁺Cl⁻ are obtained. For preparing a compound I wherein R¹ is methyl or ethyl the following reaction is carried out.

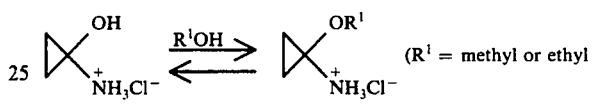 (R¹ = methyl or ethyl

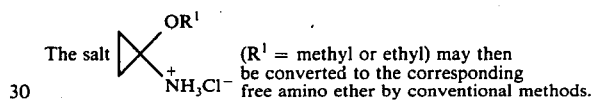

The salt (R¹ = methyl or ethyl) may then be converted to the corresponding free amino ether by conventional methods.

The reaction scheme below exemplifies the reaction sequences:

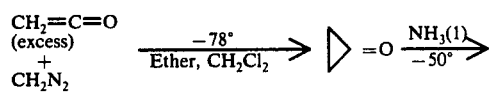 a)

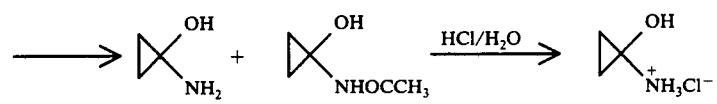

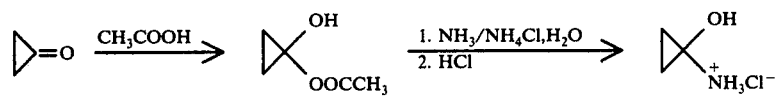 b)

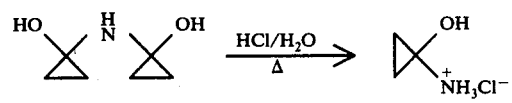 c)

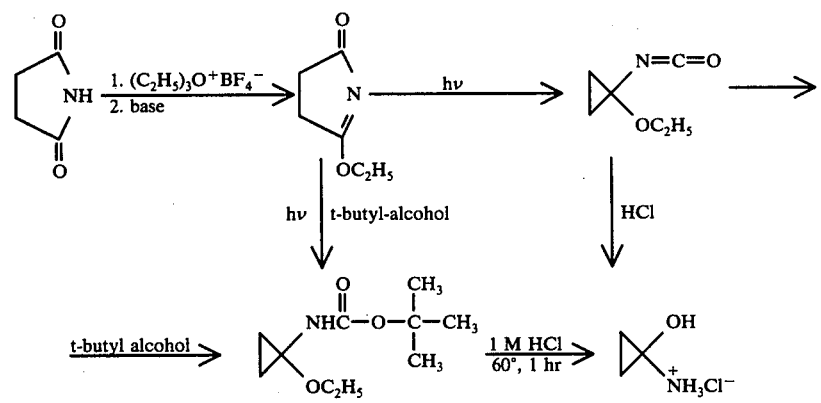

-continued

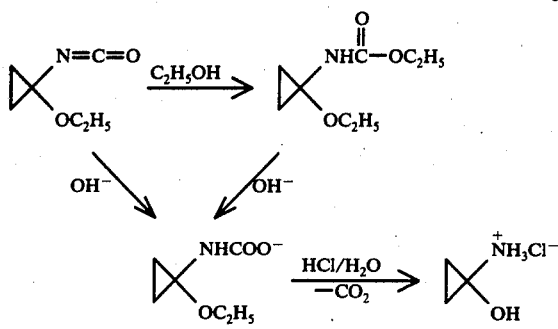

e)

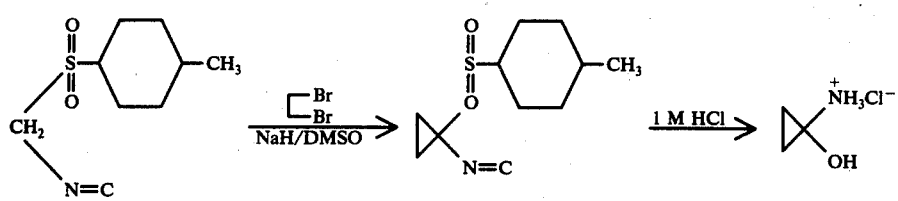

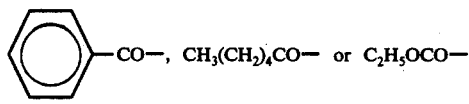 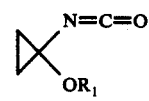

g)

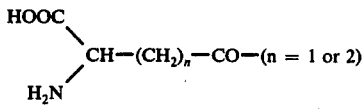

B. a. The compounds of the formula I wherein $R^2$ is the group

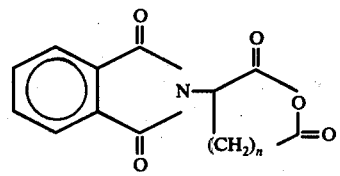

can be prepared by reaction

wherein $R^1$ is hydrogen, a methyl or an ethyl group with a functionally equivalent derivative of $R^2$—OH. The reaction is performed in the presence of a base, preferably triethylamine and a suitable solvent, such as tetrahydrofuran. The amine to be acylated may be preformed or liberated in situ by employing a salt such as its hydrochloride in the reaction above. The functionally equivalent derivative of $R^2$—OH should be able to acylate a primary amino group. Such functional equivalents include acid chlorides, acid bromides, acid azides, activated esters, acid anhydrides, mixed acid anhydrides, particularly the mixed anhydrides prepared from stronger organic acids such as the lower aliphatic monoesters of carbonic acid, and mixed anhydrides prepared form inorganic acids such as dichlorophosphoric acid. In addition an activated heterocyclic amide such as an imidazolide may be used or the free acid itself may be coupled with the amino cyclopropane compound by the use of a carbodiimide reagent or other compounds such as N-ethyl-5-phenylisoxazolium-3-sulphonate, which can promote the formation of an amide upon addition to a mixture of an acid and an amine.

b. The compounds of the formula I wherein $R^1$ is a hydrogen atom, a methyl group or an ethyl group and $R^2$ is the group $C_2H_5OCO$ can also be prepared by reaction with ethanol of wherein $R^1$ is a methyl or an ethyl group, giving the desired products, wherein $R^1$ is a methyl or ethyl group, which is then, if desired, converted by partial acid hydrolysis to the product wherein $R^1$ is hydrogen.

C. The compounds of the formula I wherein $R^2$ is the group $$HOOC\diagdown CH-(CH_2)_n-CO-(n = 1\ or\ 2)$$
$$H_2N\diagup$$

can be prepared in two steps by reaction of a compound of the formula with a compound of the formula wherein $R^1$ is hydrogen, methyl or ethyl, essentially as described under B.a) and subsequent de-blocking of the amino group (for instance by treatment with hydrazine).

The reaction scheme below exemplifies the reaction sequences:

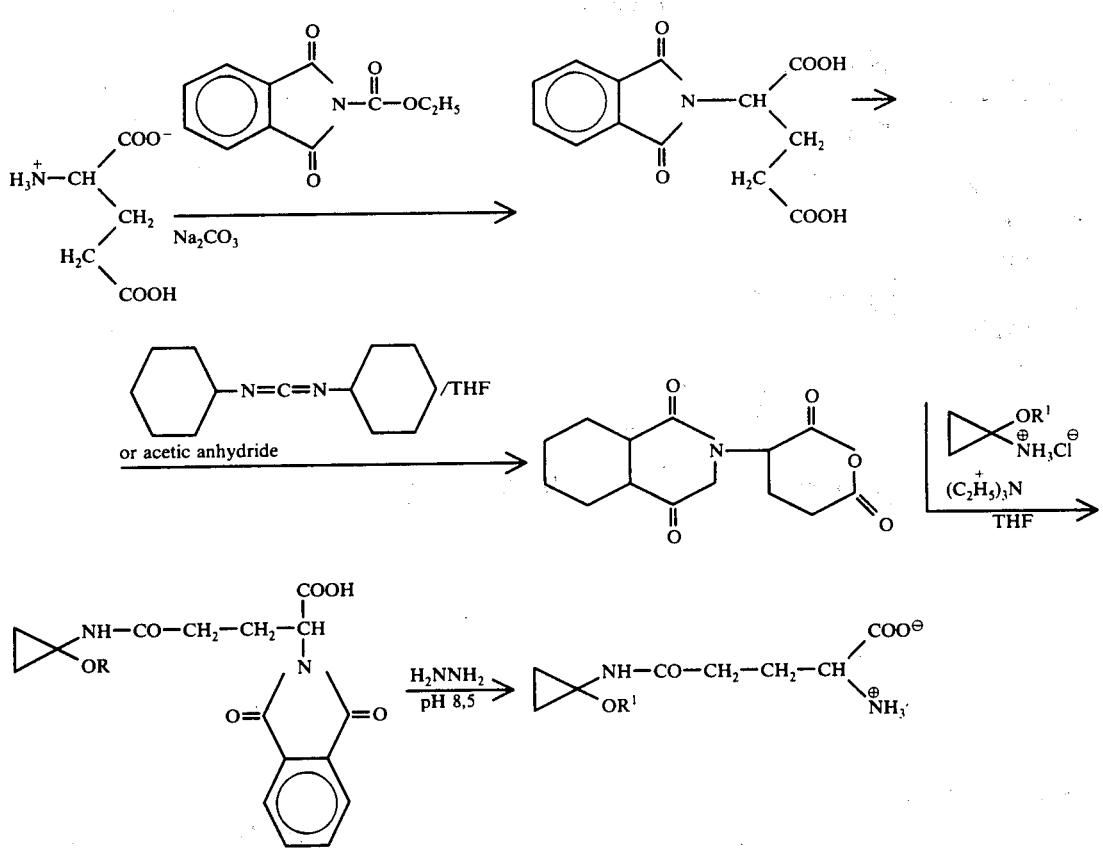

D. The compounds of the formula I wherein $R^2$ is $$HOOC-(CH_2)_n-\underset{\underset{NH_2}{|}}{CH}-CO- \quad (n = 1 \text{ or } 2)$$

can be prepared by reaction of a compound of the formula

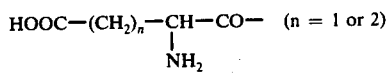

wherein $Z^2$ is a tertiary butoxy group or a trifluoromethyl group, with an acid. The reaction scheme below exemplifes the reaction sequences:

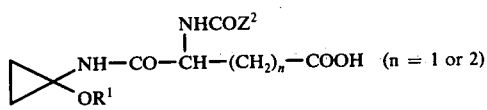

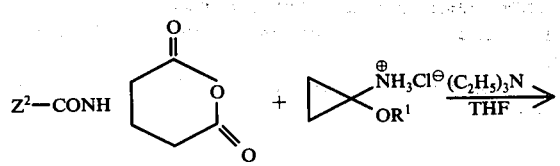

E. The compound of the formula

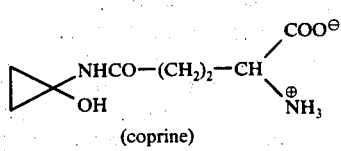

(coprine)

can also be obtained by isolation from the fungus *Coprinus atramentarius*.

The isolation is started with the preparation of an ethanol extract of the fungus. The extract is freed from lipids and then dialysed. The dialysed product is subjected to chromatography on a strongly acidic cation-exchange column. The acidic amino acids are then eliminated on an acetate-saturated anion exchanger. Coprine can then be obtained by crystallization. The various steps of the isolation are evident from the scheme below:

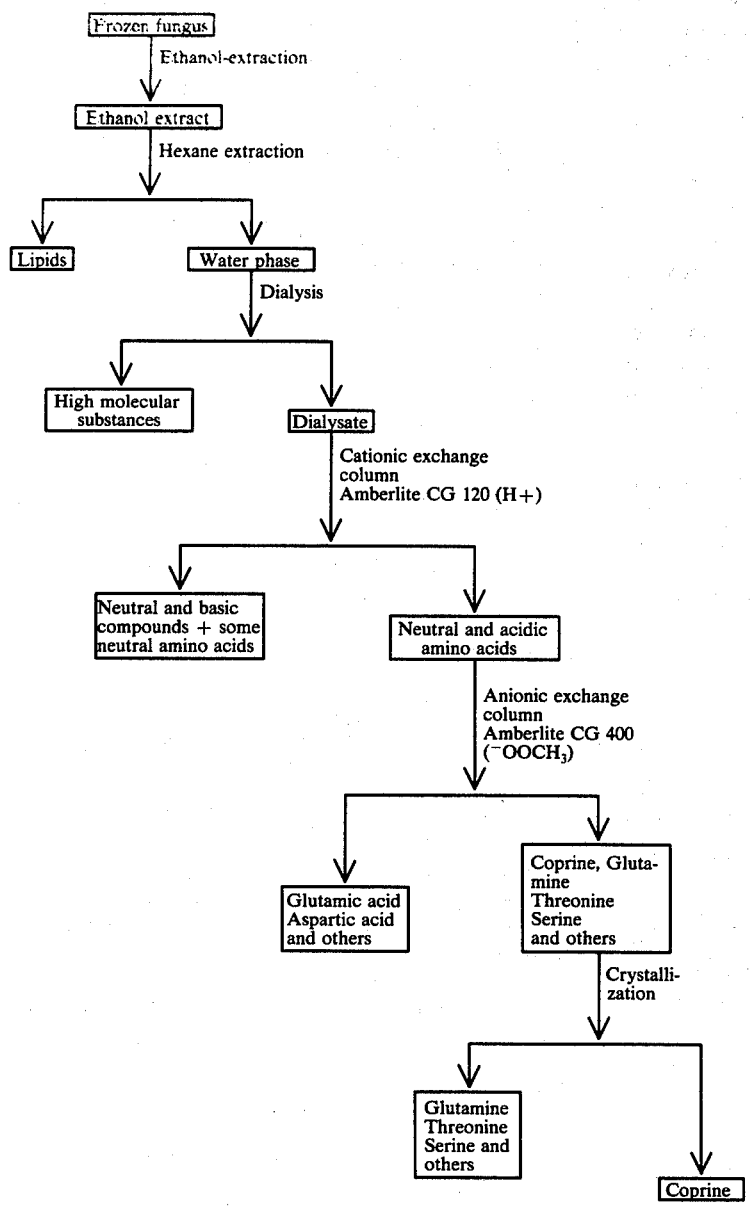

e. Intermediates

For the preparation of the compounds of the formula I wherein $R^2$ is a group

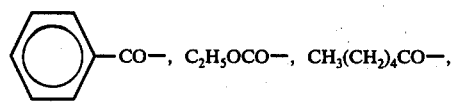

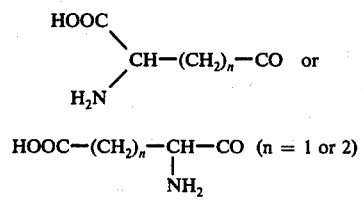

$HOOC-(CH_2)_n-\underset{\underset{NH_2}{|}}{CH}-CO$ (n = 1 or 2)

it has been found that a compound of the formula

wherein $R^1$ is hydrogen, a methyl or ethyl group is a valuable intermediate.

The preparation of these compounds is described previously in this application.

f. Working examples

EXAMPLE 1,1-hydroxycyclopropylammonium chloride

Method A, a.

A cooled (−78°) solution of diazomethane (0.1 mol) in ether (200 ml) is added with vigorous stirring to a solution of ketene (0.3 mol) in methylene chloride (400 ml, −78°). The rate of addition is adjusted to keep the temperature below −60°. The greater part of the ketene excess is then evaporated (1 mm Hg, −70°) and liquid ammonia (40 g, 2.4 mol) saturated with NH₄Cl is rapidly added with thorough stirring. Most of the NH₃-excess is evaporated in the same way as the ketene. The temperature is then raised to −50°, and 6M HCl is added until the mixture is acid. The organic solvents are evaporated under reduced pressure. According to MNR the remaining water solution contains in addition to ammonium chloride and acetamide 3 compounds; 1-hydroxycyclopropylammonium chloride, N-(1-hydroxycyclopropyl)-acetamide and bis(1-hydroxycyclopropyl)-ammonium chloride. (The N-(1-hydroxycyclopropyl)acetamide can be extracted from the acidic mixture with either but it will then be contaminated with acetamide). After making the mixture 3M with respect to HCl and holding it at 80° for 30 minutes there remains only the 1-hydroxycyclopropylammonium chloride. In addition acetic acid and propionic acid are formed; the composition of the product mixture remains unchanged even after heating for several hours. After evaporation a mixture of 1-hydroxycyclopropylammonium chloride and NH₄Cl remains. These two components can be separated by extraction with butanol according to example 2 below.

EXAMPLE 2, 1-hydroxycyclopropylammonium chloride

Method A, b.

1-Acetoxycyclopropanol (440 mg, 3.8 mmol) [W.J.M. van Tilborg, Thesis, Amsterdam 1971] is added to a solution of ammonium chloride (205 mg, 3.8 mmol) in 25% ammonia solution (600 mg, 8.8 mmol NH₃). The mixture is acidified with conc. HCl and the precipitate is filtered off. An NMR-spectrum on the filtrate indicates the presence of bis(1-hydroxycyclopropyl)-ammonium chloride, 1-hydroxycyclopropylammonium chloride and 1,1-dihydroxycyclopropane. After further acidification (to 4M HCl) and heating at 90° for 15 min there remains 1-hydroxycyclopropylammonium chloride, propionic acid, acetic acid and ammonium chloride. After evaporation in vacuo, the residue is extracted several times with hot n-butanol. The butanol solution is evaporated in vacuo. Water is added to the residue and then evaporated. This procedure is repeated several times which yields, as an oil, 1-hydroxycyclopropylammonium chloride (116 mg, 28%); NMR (60 MHz): $\delta^{D_2O}$ = 1.17 (s, 4H).

EXAMPLE 3,
1-HYDROXYCYCLOPROPYLAMMONIUM CHLORIDE

METHOD A, c.

To bis(1-hydroxycyclopropyl)-amine (50 mg) [W. J. M. van Tilborg, Thesis, Amsterdam 1971] in D₂O is added a small excess of conc. HCl. The NMR-spectrum shows a singlet for bis(1-hydroxycyclopropyl)-ammonium chloride ($\delta^{D_2O}$ = 1.25 (s, 4H)). The sample is heated at 80° for 4 hr yielding 1-hydroxycyclopropylammonium chloride ($\delta^{D_2O}$ = 1.17 (s, 4H)) and propionic acid. (The decomposition is much faster at higher HCl concentrations). Evaporation gives, as an oil, 1-hydroxycyclopropylammonium chloride.

EXAMPLE 4,
1-HYDROXYCYCLOPROPYLAMMONIUM CHLORIDE

METHOD A, d. from
N-(1-Hydroxycyclopropyl)-acetamide.

N-(1-hydroxycyclopropyl)-acetamide (prepared by reaction of 1-hydroxycyclopropylammonium chloride with acetic anhydride in the presence of triethylamine; mp 81°-85°; NMR (60 MHz): $\delta^{CDCl_3}$ = 0.70–1.26 (m, 4H), 1.98 and 2.26 (2s, total 3H), 5.0 (br. s, 1H), 7.2 (br. s, 1 H), (two rotamers)) is dissolved in 2M HCl and heated at 80° for 1 hr. This treatment hydrolyses all starting material to 1-hydroxycyclopropylammonium chloride and acetic acid (NMR). Evaporation gives as an oil 1-hydroxycyclopropylammonium chloride in quantitative yield.

EXAMPLE 5,
1-HYDROXYCYCLOPROPYLAMMONIUM CHLORIDE METHOD A, d. From
N-(1-ethoxycyclopropyl)-t-butyl carbamate.

N-(1-Ethoxycyclopropyl)-t-butyl carbamate [T. H. Kock and R. J. Sluski; Tetrahedron Lett., 2391 (1970)] is treated with 1M HCl at 60° for 1 hr. The solution is evaporated in vacuo yielding pure 1-hydroxycyclopropylammonium chloride as an oil (quantitative yield).

EXAMPLE 6,
1-METHOXYCYCLOPROPYLAMMONIUM CHLORIDE

METHOD A, d. From
N-(1-ethoxycyclopropyl)-t-butyl carbamate.

N-(1-ethoxycyclopropyl)-t-butyl carbamate (12 g, 59.7 mmol) is treated with 2M HCl (150 ml) at 60° for 1 hr. The solution obtained is evaporated in vacuo. Dry methanol (100 ml) is added and the solution is evaporated. This is repeated three times. The final evaporation is interrupted when a few ml of solvent remain and abs. ether is added, precipitating 1-methoxycyclopropylammonium chloride. After cooling, filtering and washing with abs. ether, pure 1-methoxycyclopropylammonium chloride is obtained, mp 106°-108° (5.2, 71%); NMR (60 MHz): $\delta^{CDCl_3}$ = 0.97–1.47 (m, 4H), 3.55(s, 3H), 8.9(br. s, 3H).

EXAMPLE 7,
1-ETHOXYCYCLOPROPYLAMINE

Method A, d. From N-(1-ethoxycyclopropyl)-t-butyl carbamate.

N-(1-Ethoxycyclopropyl)-t-butyl carbamate (4.0 g, 19.9 mmol) is treated with 2M HCl (50 ml) at 60° for 1 hr and the solution is evaporated in vacuo. Abs. ethanol is added and evaporated 4 times. The final evaporation is interrupted when a few ml of solvent remain and abs. ether (50 ml) is added, precipitating 1-ethoxycyclopropylammonium chloride. Filtering and washing with abs. ether yields pure 1-ethoxycyclopropylammonium chloride, mp 96°-98° (2.2 g, 81%); NMR(60 MHz): $\delta^{CDCl_3}$ = 0.97–1.47 (m, 4H), 1.23 (t, J=7 Hz, 3H), 3.82(q, J=7 Hz, 2H), 8.9 (br. s, 3H).

1-Ethoxycyclopropylammonium chloride (1.0 g, 7.3 mmol) is dissolved in methylamine (5 ml). Excess methylamine is evaporated and the residue is distilled, yielding pure 1-ethoxycyclopropylamine (0.5 g, 50%); NMR(60 MHz): $\delta^{CDCl_3}$ = 0.60–1.00 (m, 4H), 1.17 (t, J=7 Hz, 3H), 2.25(br. s, 2H), 3.55(q, J=7 Hz, 2H).

EXAMPLE 8,
1-HYDROXYCYCLOPROPYLAMMONIUM CHLORIDE

Method A, d. From N-(1-ethoxycyclopropyl)-benzyl carbamate.

N-(1-ethoxycyclopropyl)-benzyl carbamate (made by reacting 1-ethoxycyclopropylisocyanate with benzyl alcohol followed by distillation, $bp_{0.2}$ 118°–124° ; NMR(60 MHz): $\delta^{CDCl_3}$ = 0.79–1.27 ($m$, 4H), 1.12 ($t$, J=7 Hz, 3H), 3.60 ($q$, J=7 Hz, 2H), 5.10 ($s$, 2H), 5.85 (br. $s$, 1H), 7.32 ($s$, 5H)) is treated with excess of 2 M HCl at 90° for 5 hr. Evaporation of the aqueous phase, after extraction with chloroform, yields 1-hydroxycyclopropylammonium chloride.

EXAMPLE 9,
1-HYDROXYCYCLOPROPYLAMMONIUM CHLORIDE

Method A, d. From 1-ethoxycyclopropylisocyanate.

To 1-ethoxycyclopropylisocyanate [T. H. Koch, R. J. Sluski and R. H. Moseley; JACS 95, 3957 (1973)] is added an excess of 2M HCl. The mixture is left at room temperature for 15 hr. Evaporation in vacuo gives 1-hydroxycyclopropylammonium chloride in quantitative yield.

EXAMPLE 10,
1-HYDROXYCYCLOPROPYLAMMONIUM CHLORIDE

Method A, e. From N-(1-ethoxycyclopropyl)-ethyl carbamate.

To a solution of N-(1-ethoxycyclopropyl)-ethyl carbamate (0.17 g, 1.0 mmol) in tetrahydrofuran (0.5 ml) is added 6 M NaOH (0.5 ml). The mixture is stirred at room temperature for 72 hr, water (1 ml) is added and the mixture is extracted with chloroform. (The chloroform phase contains unreacted starting material). The aqueous phase is acidified with HCl and evaporated in vacuo yielding 1-hydroxycyclopropylammonium chloride (22 mg, 20%).

EXAMPLE 11,
1-HYDROXYCYCLOPROPYLAMMONIUM CHLORIDE

Method A. f. From 1-piperidinocyclopropanol.

1-Piperidinocyclopropanol (200 mg, 1.42 mmol) is treated at room temperature for 30 min. with a solution of ammonium chloride (0.25 g, 4.7 mmol) in 20% ammonia solution (2.0 g, 29.6 mmol $NH_3$). The mixture is acidified with conc. HCl and the precipitate is filtered off. (NMR-spectrum of the filtrate corresponds to a mixture of 1-hydroxycyclopropylammoniun chloride and unreacted starting material). The product is purified by extraction of the solution several times with methylene chloride followed by evaporation of the aqueous phase containing 1-hydroxycyclopropylammonium chloride and $NH_4Cl$. By using the butanol extraction procedure described in example 2 above, pure 1-hydroxycyclopropylammonium chloride (8 mg, 5%) is obtained.

EXAMPLE 12,
1-HYDROXYCYCLOPROPYLAMMONIUM CHLORIDE

Method A, g. From p-tosylmethyl isocyanide (TosMIC).

Sodium hydride (ca 50% in oil; 0.96 g, ca 20 mmoles) is reacted with dry dimethyl sulfoxide (5 ml) in tetrahydrofuran (25 ml; sodium-dried) for 1 hour at room temperature. The mixture is cooled to 0°, 1,2-dibromoethane is added quickly and TosMIC [A. M. van Leusen et al; Tetrahedron Letters, 2367 (1972)] (1.96 g, 10 mmoles) in tetrahydrofuran (25 ml) is added dropwise (30 min) at 0°. After 2 hours at room temperature the precipitate is filtered off and the filtrate is evaporated to dryness. The residue is dissolved in methylene chloride (100 ml) and the solution is washed with water (4×25 ml). The organic phase is dried over $Na_2SO_4$ and is applied to an $Al_2O_3$-column, which then is eluted with methylene chloride. The eluate is evaporated to dryness and the residue is dissolved in a minute amount of hot methanol. When the solution is cooled to 0° the product crystallizes out. Filtering and washing with cold ether yields pure 1-p-tosylcyclopropyl isocyanide, mp 126°–127° (1.3 g; 59%); NMR (60 MHz): $\delta^{CDCl_3}$=1.43–2.05 ($m$, 4H), 2.45 ($s$, 3H), 7.41–8.0 ($m$, 4H).

1-p-tosylcyclopropyl isocyanide (1.9 g, 8.6 mmoles) is treated with 1M HCl (40 ml) for 2 hours at 60°. The solution obtained is cooled to 0° and the precipitated p-toluene sulfinic acid is filtered off and washed with ice-cold 1M HCl. The filtrate is heated at 60° (30 min), which forms more sulfinic acid that is separated in the same way as described above. The filtrate thus obtained (ca 60 ml) is extracted with methylene chloride (3×10 ml) and the organic phase is discarded. Pure 1-hydroxycyclopropyl ammonium chloride is obtained by filtering the water phase through an anion exchanger (Amberlite CG-4B; 200–400 mesh, AcO -saturated) into 1M HCl followed by evaporation of the eluate in vacuo, or by preparing 1-ethoxycyclopropylammonium chloride according to example 7 followed by hydrolysis of this crystalline compound and evaporation in vacuo (710 mg; 75%).

EXAMPLE 13,
N-(1-HYDROXYCYCLOPROPYL)-BENZAMIDE

Method B, a.

Benzoyl chloride (4.2 g, 30 mmol) is added to a suspension of 1-hydroxycyclopropylammonium chloride (2.67 g, 24.5 mmol) in dry tetrahydrofuran. Triethylamine (6.5 g, 65 mmol) is added dropwise with stirring and ice-cooling (1 hr). The precipitate is filtered off and washed with tetrahydrofuran. The filtrate obtained is evaporated in vacuo. The crystalline residue is recrystallised from chloroform yielding N-(1-hydroxycyclopropyl)-benzamide, mp 153°–155° (3.0 g, 69%); NMR=$\delta^{CDCl_3}$=0.87–1.38 ($m$, 4H), 4.7 (br. $s$, 1H), 7.3–7.9 ($m$, 6H, incl. NH).

EXAMPLE 14,
N-(1-METHOXYCYCLOPROPYL)-BENZAMIDE

Method B, a.

Triethylamine (3.1 g, 30.5 mmol) is added dropwise (30 min) at 0° to a solution of benzoyl chloride (1.5 g, 12.2 mmol) in tetrahydrofuran (25 ml) containing suspended 1-methoxycyclopropylammonium chloride (1.82 g, 13.0 mmol). The mixture is then stirred at room temperature for 30 min. The precipitate is filtered off and washed thoroughly with tetrahydrofuran. The filtrate is evaporated in vacuo yielding a crystalline residue. Recrystallisation from methanol gives pure N-(-methoxycyclopropyl)-benzamide, mp 190°–191° (1.2 g, 55%); NMR (60 MHz)=$\delta^{CDCl_3}$=1.00–1.30 (m, 4H), 3.40 (s, 3H), 7.0 (br. s, 1H), 7.35–7.95 (m, 5H).

EXAMPLE 15,
N-(1-ETHOXYCYCLOPROPYL)-BENZAMIDE

Method B, a.

Triethylamine (2.5 g, 25 mmol) is added dropwise at 0° to a solution of 1-ethoxycyclopropylammonium chloride (1.25 g, 9.15 mmol) and benzoyl chloride (1.4 g, 10 mmol) in dry tetrahydrofuran (20 ml). The precipitate is filtered off and the filtrate is evaporated in vacuo yielding a crystalline residue. Sublimation following by recrystallisation from cyclohexane gives N-(1-ethoxycyclopropyl)-benzamide, mp 108°–109° (0.95 g, 51%); NMR (60 MHz): $\delta^{CDCl_3}$ = 0.90–1.38 (m, 4H), 1.16 (t, J=7 Hz, 3H), 3.77 (q, J=7 Hz, 2H), 7.0–8.0 (1 m and 1 br. s, total 6H).

EXAMPLE 16,
N-(1-ETHOXYCYCLOPROPYL)-CAPROIC AMIDE

Method B, a.

Triethylamine (2.22 g, 22 mmol) is added dropwise (15 min) with vigorous stirring at 0° to a solution of 1-ethoxycyclopropylammonium chloride (1.37 g, 10 mmol) and caproyl chloride (1.34 g, 10 mmol) in dry tetrahydrofuran (30 ml) and the mixture is stirred at room temperature for 1 hr. The precipitate is filtered off and the filtrate is evaporated in vacuo. The crystalline residue (1.85 g) is dissolved in petroleum ether (20 ml) and the solution is filtered through a short silica-gel column (2 cm × 10 cm). After evaporation the residue (1.30 g) is recrystallised from petroleum ether (at low temperature) yielding pure N-(1-ethoxycyclopropyl)-caproic amide, mp 47°–48.5° (1.0 g, 50%); NMR (60 MHz): $\delta^{CDCl_3}$ = 0.7–1.9 (m, 16H), 2.0–2.4 and 2.4–2.8 (2 m, total 2H), 3,57 and 3.63 (2q, J=7.2 Hz, total 2H), 6.7 (br. s, 1H), (two rotamers).

EXAMPLE 17,
N-(1-METHOXYCYCLOPROPYL)-ETHYL CARBAMATE

Method B, a.

Triethylamine (2.55 g, 2.5 mmol) in dry tetrahydrofuran (20 ml) is added dropwise (30 min) at 0° with stirring to a solution of chloroethyl formate (1.13 g, 10.5 mmol) in dry tetrahydrofuran (30 ml) containing suspended 1-methoxycyclopropylammonium chloride (1.23 g, 10 mmol). The mixture is then stirred at room temperature for 1 hr. The precipitate is filtered off and the filtrate is evaporated in vacuo. The residue id distilled (vigreux column) yielding pure N-(1-methoxycyclopropyl)-ethyl carbamate; NMR (60 MHz): $\delta^{CDCl_3}$ = 0.79–1.23 (m, 4H), 1.24 (t, J=7 Hz, 3H), 3.32 (s, 3H), 4.13 (q, J = 7Hz, 2H), 6.0 (br. s, 1H).

EXAMPLE 18,
N-(1-ETHOXYCYCLOPROPYL)-ETHYL CARBAMATE

Method B, a.

Triethylamine (2.55 g, 2.5 mmol) in dry tetrahydrofuran (20 ml) is added dropwise (30 min) at 0° with stirring to a solution of chloroethyl formate (1.13 g, 10.5 mmol) in dry tetrahydrofuran (30 ml) containing suspended 1-ethoxycyclopropylammonium chloride (1.37 g, 10 mmol). The mixture is stirred at room temperature for 1 hr. The precipitate is filtered off and the filtrate is evaporated in vacuo. The residue is distilled (vigreux column) yielding N-(1-ethoxycyclopropyl)-ethyl carbamate, $bp_{0.8}$ 69° (1.5 g, 86%); NMR (60 MHz): $\delta^{CDCl_3}$ = 0.79–1.23 (m, 4H), 1.13 (t, J=7 Hz, 3H), 1.24 (t, J=7 Hz, 3H), 3.64 (q, J=7 Hz, 2H), 4.13 (q, J=7 Hz, 2H), 5.85 (br. s, 1H).

EXAMPLE 19
N-(1-HYDROXYCYCLOPROPYL)-ETHYL CARBAMATE

Method B, b.

a. Abs. ethanol (2.0 g, 43.5 mmol) with triethylamine (3 drops) is added to 1 -ethoxycyclopropylisocyanate (1.53 g, 12.1 mmol) and the mixture is left at 40° for 1 hr. Pentane (2ml) is added, the mixture is cooled with ice and the precipitate, consisting of N,N'-bis (1-ethoxycyclopropyl)-urea (90 mg), is filtered off. The filtrate is evaporated and the residue distilled, yielding pure N-(1-ethoxycyclopropyl)-ethyl carbamate, $bp_{0.8}$ 69° (1.64 g, 78%); NMR (60 MHz): $\delta^{CDCl_3}$ = 0.79–1.23 (m, 4H), 1.13 (t, J=7Hz, 3H), 1.24 (t, J=7 Hz, 3H), 3.64 (q, J=7Hz, 2H), 4.13 (q, J=7Hz, 2H, 5.85 (br. s, 1H).

b. A solution of N-(1-ethoxycyclopropyl)-ethyl carbamate (100mg, 0.58 mmol) in 2 M HCl (1 ml) is heated at 90° for two min. The solution is evaporated in vacuo yielding N-(1-hydroxycyclopropyl)-ethyl carbamate (67.5 mg, 80%); NMR (60 MHz): $\delta^{CDCl_3}$ = 0.79–1.23 (m, 4H), 1.24 (t, 3H), 2.8 (br. s, 1H), 4.13 (q, 2H), 6.4 (br. s, 1H).

EXAMPLE 20,
COPRINE($N^5$-(1-HYDROXYCYCLOPROPYL)-L-GLUTAMINE)

Method C.

Triethylamine (14.0 g, 0.135 mol) dissolved in dry tetrahydrofuran (75 mol) is added dropwise (1hr) to an icecooled solution of phthaloyl-L-glutamic acid anhydride (35.0 g, 0.135 mol) [Nefkens et al; Rec. Trav. Chim. 79, 688 (1960)] in tetrahydrofuran (225 ml) containing suspended 1-hydroxycyclopropylammonium chloride (13.6 g, 0.124 mol). The mixture is stirred for 1 hr at room temperature, the precipitate is filtered off and the filtrate is evaporated in vacuo. The residue is dissolved in water (500 ml) with the aid of sodium carbonate (to pH 7). Hydrazine hydrate (7.5 g, 0.15 mol) is added and the mixture is left at room temperature for 4 hr, and then acidified (to pH 1.5) with conc. HCl. The phthaloylhydrazide crystallises out on standing overnight and is filtered off. The filtrate is eluted through a cation-exchange column (Amberlite CG 120, 200–400 mesh, 50 cm × 3 cm, H+-form). The column is washed with water and eluted with 0.3M sodium hydroxide (displacement chromatography). The fractions containing coprine are combined and passed through an acetate-saturated anion exchanger (Amberlite CG 4B, 200–400 mesh, 10 cm × 4 cm) to eliminate glutamic acid and some other impurities. Evaporation of the eluate yields a crystalline residue (16 g), which is practically pure coprine. Recrystallisation from water-ethanol gives pure coprine, mp 197°–199° (14.0 g, 56%); $[\alpha]_D^{25} = +7.6°$; NMR (100 MHz): $\delta^{D_2O} = 0.81-1.14$ (m, 4H), 1.99–2.24 (m, 2H, H$_2$C-3), 2.31–2.49 (m, 2H, H$_2$C-4), 3.77 (t, 1H, HC-1).

EXAMPLE 21,
O-ETHYLCOPRINE
(N$_5$-(1-ETHOXYCYCLOPROPYL)-L-GLUTAMINE)

Method C.

Triethylamine (7.6 g, 76.5 mmol) dissolved in dry tetrahydrofuran (50 ml) is added dropwise (30 min) to an ice-cooled solution of phthaloyl-L-glutamic acid anhydride (19.8 g, 76.5 mmol) and 1-ethoxycyclopropylammonium chloride (10.5 g, 76.5 mmol) in dry tetrahydrofuran (250 ml). The precipitate is filtered off and the filtrate is evaporated in vacuo. The residue is dissolved in water (500 ml) with the aid of sodium carbonate (to pH 8). Hydrazine hydrate (4.0 g, 80 mmol) is added and the mixture is left at room temperature for 4 hr, and then acidified (to pH 1.5) with conc. HCl. The phthaloyl hydrazide crystallises out on standing overnight and is filtered off. The filtrate is eluted through a cation-exchange column (Amberlite CG 120, 200–400 mesh, 40 cm × 2.5 cm, H$^+$-form). The column is washed with water and eluted with 0.3M sodium hydroxide (displacement chromatography). The fractions containing 0-ethylcoprine are combined and passed through an acetate-saturated anion exchanger (Amberlite CG 4B, 200–400 mesh, 10 cm × 4 cm) to eliminate glutamic acid and other impurities. Evaporation of the eluate yields a crystalline residue (12 g), which is practically pure 0-ethylcoprine. Recrystallisation from water-ethanol-acetone-ether gives pure 0-ethylcoprine, mp 183°–184° (10.5 g, 59.5%); $[\alpha]_D^{25} = +5.2°$ (H$_2$O); NMR (60MHz): $\delta^{D_2O} = 0.73-1.25$ (m, 4H), 1.12 (t, J=7.2 Hz, 3H), 1.84–2.62 (m, 4H), 3.60 (q, J=7.2 Hz, 2H), 3.71 (t, J=6.0 Hz, 1H).

EXAMPLE 22,
N$^4$–(1-HYDROXYCYCLOPROPYL)-L-ASPARAGINE

Method C

Triethylamine (5.5 g, 54.5 mmol) in dry tetrahydrofuran (50 ml) is added dropwise (30 min) at 0° with stirring to a solution of phthaloyl-L-aspartic acid anhydride (12.3 g, 50 mmol) in dry tetrahydrofuran (200 ml) containing suspended 1-hydroxycyclopropylammonium chloride (5.45 g, 50 mmol). Stirring is continued at room temperature for 1 hr. The precipitate is filtered off and the filtrate is evaporated in vacuo. The residue is dissolved in water (200 ml) with the aid of sodium carbonate (to pH 7). Hydrazine hydrate (3.0 g, 60 mmol) is added and the mixture is left at room temperature for 4 hr, and then acidified (to pH 1.5) with conc. HCl. The phthaloyl hydrazide crystallises out on standing overnight and is filtered off. The filtrate is eluted through a cation-exchange column (Amberlite CG 120, 200–400 mesh, 35 cm × 3 cm). The column is washed with water and eluted with 0.3M sodium hydroxide (displacement chromatography). The fractions containing N$^4$–(1-hydroxycyclopropyl)-L-asparagine (TLC: BuOH-acetone-H$_2$O-Et$_2$NH, 10:5:5:3/cellulose, $r_f$=0.36, orange spot with ninhydrin) are combined and passed through an acetate-saturated anion exchanger (Amberlite CG 4B, 200–400 mesh, 10 cm × 3 cm) to eliminate aspartic acid and other impurities. Evaporation of the eluate yields a crystalline residue which on crystallisation from water-ethanol gives pure N$^4$–(1-hydroxycyclopropyl)-L-asparagine (1.0 g. 10.5 %); NMR (60 MHz): $\delta^{D_2O} = 0.75-1.22$ (m, 4H), 2.70–2.97 (m, 2H), 4.00 (dd, J$_1$=5.0 Hz, J$_2$=6.6 Hz, 1H). The main by-product is the isomer N$^1$–(1-hydroxycyclopropyl)-L-isoasparagine (NMR (60 MHz): $\delta^{D_2O} = 0.75-1.22$ (m, 4H), 2.63–2.90 (m, 2H), 4.15 (dd, J$_1$=5.7 Hz, J$_2$=7.0 Hz, 1H).

EXAMPLE 23,
ISOCOPRINE
(N$^1$-(1-HYDROXYCYCLOPROPYL)-L-ISO-GLUTAMINE)

Method D.

Triethylamine (20.2 g, 0.20 mol) in tetrahydrofuran (100 ml) is added dropwise (30 min) at 0° to a solution of trifluoroacetamido- L-glutamic acid anhydride (49.5 g, 0.22 mol) [Weygand und Reiher; Ber 88, 26 (1955)] in tetrahydrofuran (400 ml) containing suspended 1-hydroxycyclopropylammonium chloride (21.8 g, 0.20 mol). The mixture is stirred at room temperature for 1 hr. The precipitate is filtered off and the filtrate is evaporated in vacuo. To the residue is added 12 % ammonia solution (400 ml). After 24 hr at room temperature the ammonia is evaporated in vacuo (25° ). Water (400 ml) is added and the solution is filtered through a cation-exchange column (Amberlite CG 120, 200–400 mesh, 50 cm × 2,5 cm, H$^+$-form). The column is washed with water and eluted with 0.3M sodium hydroxide (displacement chromatography). The fractions containing isocoprine (TLC: BuOH-acetone-H$_2$O-Et$_2$NH, 10:5:5:3/cellulose, $r_f$ =0.30, yellow spot (later blue) with ninhydrin) are combined and passed through an acetate-saturated anion exchanger (Amberlite CG 4B, 200–400 mesh, 10 cm × 4 cm). The eluate is evaporated to dryness in vacuo. Crystallisation from methanol-ethanol gives isocoprine (4.0 g, 10 %); NMR (60 MHz): $\delta^{D_2O} = 0.77-1.26$ (m, 4H), 1.86–2.50 (m, 4H), 3.95 (t, 1H).

EXAMPLE 24, COPRINE
(N$^5$-(1-HYDROXYCYCLOPROPYL)-L-GLUTAMINE

Method E.

Frozen fresh mushrooms (65.2 kg) are minced in a turmix with 95 % ethanol (62.1). The slurry is mixed with celite and the filter cakes are pressed (20 kp/cm$^2$). The extract obtained is evaporated under reduced pressure (bath temp 40°). The residue is diluted with water to about 5 l and extracted with hexane (3 × 2.5 l). The extract is discarded. The water phase (dry weight: 1.5 kg) is dialysed stepwise against pure water (total high molecular weight residue: 78 g). The dialysable material (in 93 l of solution) is subjected without prior concentration to displacement chromatography on a strongly acidic cation exchanger (Amberlite CG 120, 200–400 mesh). The solution is processed in 7 equal batches on ion exchange columns of dimensions 8 cm diam × 15 cm height. After adding the sample the column is washed with water and eluted with 0.15 M NaOH until the visible alkaline front begins to emerge. The acidic amino acids, which are eluted first, and the greater part of the neutral amino acids, are combined (total 120 g)

and rechromatographed (0.25 M NaOH) on a somewhat longer column (8 cm diam × 21 cm). The fractions containing coprine, together with glutamic acid, aspartic acid, threonine and part of the serine are crystalline (total 60.5 g). Glutamic acid, aspartic acid and some other acidic compounds (13.2 g) are eliminated by a passage through an acetate-saturated anion exchanger (Amberlite CG 400, 200–400 mesh, 8 cm diam × 6 cm). The eluates are combined and concentrated giving a crystalline residue (23.6 g). Recrystallisation of this material several times from water-ethanol aided by further ion exchange displacement chromatography of the mother liquors gives pure coprine, mp 197°–199° (7.3 g); $[\alpha]_D^{25} = +7.6°$ (H$_2$O); NMR (100 MHz): $\delta^{D_2O}$ = 0.81–1.14 (m, 4H), 1.99–2.24 (m, 2H, H$_2$C-3), 2.31–2.49 (m, 2H, H$_2$C-4), 3.77 (t, 1H, HC-2).

g. Pharmacological tests

Ethanol is converted in vivo, to acetic acid according to the following sequence

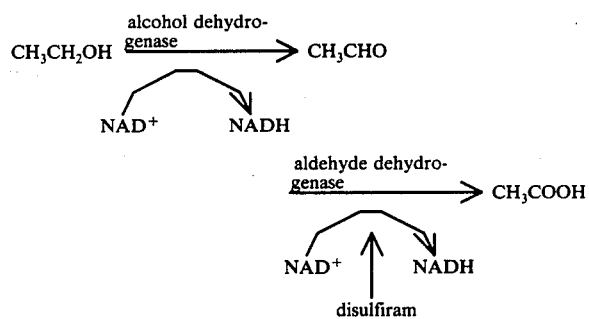

A. Compounds of this invention have been tested in order to study their interaction with the metabolism of ethanol in rats. The compounds have been found to increase the gas-chromatographically determined ratio acetaldehyde/ethanol in rat breath samples. This is interpreted to result from an inhibition of acetaldehyde dehydrogenase.

Procedure for experiments involving oral feeding.

Male Sprague-Dawley rats, 170–370 g, were starved over night with free access only to water. The next morning the drug was administered as an aqueous solution (in 0.9% saline) by means of a rubber feeding tube, which was passed down the oesophagus to the stomach. The dose volume was in all but a few cases 10 ml/kg. Due to a lower solubility of N-(1-hydroxycyclopropyl)-benzamide and its ethyl ether a dose volume of 20 ml/kg had to be used for the higher doses of these compounds. In the case of the caproamide derivative a 1:1 mixture of ethanol and 0.9% saline had to be used as the vehicle.

Six hours later, ethanol (3 g/kg) was administered by the same technique, as an aqueous solution (20% w/v). The dose volume was 15 ml/kg. During the time-period of 30–45 minutes after administration of ethanol, three breath samples were taken from the rats. The rats were forced to breath for thirty seconds into a rubber tube (25ml). A gas sample of about six milliliters was withdrawn through the rubber wall with the help of a gastight 10 ml Hamilton syringe. The tube and syringe were rinsed with nitrogen after each collection. Five milliliters of the gas sample was injected into a gas chromatograph (Hewlett-Packard 5711) equipped with a column (⅛ inch × 2 m) packed with 50–80 mesh Porapak N. The column temperature was 160° C and the carrier gas (N$_2$) flow rate was 30 ml/min. The sensitivity of the instrument was checked every day before and after the set of experiments by injecting 500 μl of a standard gas mixture containing 100 mg/ml each of ethanol and acetaldehyde. In the animal experiments peak heights were measured and the ratio acetaldehyde/ethanol was calculated. The mean value of the three measurements on each animal was computed, and this value is given in Table 1.

Table 1

| Compound Name | Acetaldehyde/Ethanol × 10³ measured in experiments involving per os administration | | | | | |
|---|---|---|---|---|---|---|
| | Dose (mg/kg) | | | | | |
| | 1 | 3 | 9 | 27 | 81 | 243 |
| Coorine | | 0 | 13.5 | 29.5,38.2 | 61.4 | 82.9,153 |
| Ethylcoprine | | | 0 | 9.5,20.3 | 12.3,82.4 | 81.4 |
| ▷〈OH, H | | | 1.6 | 1.2,2.2 | 22.1,46.1 | |
| ▷〈OH, OH | | 3.5,7.7,25.6 | 18.7,47.7 | 13.4,40.7 | 30.0,86.3 | |
| ▷〈OAc, OAc | | | 1.7,4.6 | 32.6,54.4 | 121 | |
| ▷〈OH, NHAc | | | | | | 0.0 |
| ▷〈OEt, NHAc | | | | | 0 | |
| ▷〈OH, NHBz | | | 0,4.0 | 16.0,24.9 | 28.6,44.4 | 78.6 |
| ▷〈OEt, NHBz | | | | 27.6,52.7 | 50.8,96.1 | |

Table 1-continued

Acetaldehyde/Ethanol × 10³ measured in experiments involving per os administration

| Compound Name | Dose (mg/kg) | | | | | |
|---|---|---|---|---|---|---|
| | 1 | 3 | 9 | 27 | 81 | 243 |
| 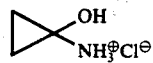 | | 0 | 15.9 | 22.1,29.1 | 21.2,75.6 | 67.7,101 |
| 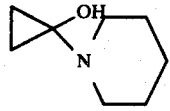 | | | 0 | 14.2 | 28.0 | 39.3 |
| 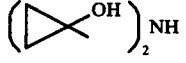 | 14.6 | 25.0 | 43.1,65.9 | 171 | 120 | |
| 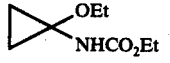 | | | | 18.8,24.5 | 42.2,73.1 | |
| 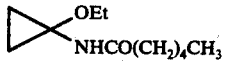 | | | 18.7 | 23.3,65.3 | 73.0 | 26.2 |

B. A comparative study of coprine and disulfiram with respect to their interaction with acetaldehyde dehydrogenase and dopamine-β-hydroxylase in the rat has been made. The gas-chromatographically determined ratio of acetaldehyde/ethanol in rat alveolar air has been taken as a measure of the degree of inhibition of aldehyde dehydrogenase, while the formation of $^{14}$C-octopamine ($^{14}$C-OA), from intravenously administered $^{14}$C-tyramine ($^{14}$C-TA), in the heart (salivary gland and thigh muscle) in the same rat was used as an indicator of the degree of dopamine-⊕-hydroxylase inhibition.

Male, Sprague-Dawley rats 150-300 g, were given the compounds to be tested intraperitoneally. Coprine was dissolved in 0.9% saline and disulfiram was suspended in saline with the aid of CMC and Tween 80 (final concentrations 1% w/v and 0.4% w/v, respectively). Ethanol, 2 g/kg (aqueous solution 20% w.v) was given intraperitoneally thirty minutes before the intravenous administation of 50 μg/kg $^{14}$C-tyramine. The alveolar air of the rats was analysed gas-chromatographically for acetaldehyde and ethanol three times during the following 15 min period, after which the rats were killed by means of concentrated chloroform vapor and the heart was dissected out, extracted in 0.4 N perchloric acid and analyzed for $^{14}$C-OA and $^{14}$C-TA.

The gas chromatographic method is described above and the estimation of β-hydroxylation of tyramine by Carlsson and Waldeck 1963 (Acta pharmacol. et toxicol. 20, 371–374).

Time-curves were established with a standard dose, 150 mg/kg i.p., of coprine and disulfiram. The mean values (± s.e.m.) of the acetaldehyde/ethanol ratios from three rats at each time interval have been calculated and are given in Table 2. From this study it is clear that the duration of the effect of coprine as well as of disulfiram on the inhibition of acetaldehyde dehydrogenase is at least 72 h in the rat. It also appears that coprine is considerably more potent than disulfiram. After 144 h the acetaldehyde/ethanol ratio is back to normal.

The effect of coprine on the formation of $^{14}$C-OA from $^{14}$C-TA was small if present (Table 3) while disulfiram lowered the yield of $^{14}$C-OA to about 10% of normal after 1 hour. There was a concomitant increase in unchanged $^{14}$C-TA. After 6h the yield of $^{14}$C-OA started to increase and was within normal limits 72 h after the administration of disulfiram.

Dose-response curves were established for two different time intervals, 2 and 18 hours, between the administration of various doses of the drug and of 2 g/kg ethanol. The mean values (± s.e.m.) for the increase in the acetaldehyde/ethanol ratio are given in Table 4. At the 2 hours interval, a dose of 81 mg/kg of disulfiram was the minimum dose which gave an increased acetaldehyde/ethanol ratio. Coprine increased the acetaldehyde/ethanol ratio even at 3 mg/kg. The dose-response curve for coprine after 18 hours was very similar to that after 2 hours, while a higher potency of disulfiram was observable at 18, as compared with 2 hrs, especially in the higher doses.

Coprine had marginal effect only on the yield of $^{14}$C-OA from $^{14}$C-TA (Table 5). In contrast, disulfiram significantly reduced the yield of $^{14}$C-DA already at a dose of 3 mg/kg when given 2 h beforehand. When given 18 h beforehand, a significant reduction in $^{14}$C-OA yield was observed first after 81 mg/kg.

It thus appears that coprine selectively blocks the aldehyde dehydrogenase while disulfiram inhibits the dopamine β-hydroxylase in addition. Moreover, coprine appears to be much more potent than disulfiram as an aldehyde dehydrogenase inhibitor.

TABLE 2

Acetaldehyde/ethanol × 10³ in rat alveolar air at various time intervals after 150 mg/kg of coprine or disulfiram. Ethanol, 2 g/kg, was given 0.5 h before the measurement. The data are the means ± s.e.m. of In general 3 experiments. Control value based on 8 experiments: 1.9 ± 0.3.

| Time (hours) | Coprine | Disulfiram |
|---|---|---|
| 1 | 50.8 ± 12.7 | 2.4 ± 0.4 |
| 2 | 49.8 ± 0.6 | 16.8 ± 4.8 |
| 4 | 90.1 ± 42.1 | 30.0 ± 14.9 |

-continued

| Time (hours) | Coprine | Disulfiram |
|---|---|---|
| 6 | 80.9 ± 12.1 | 20.2 ± 4.0 |
| 18 | 55.2 ± 4.3 | 31.2 ± 4.8 |
| 24 | 54.5 ± 1.9 | 34.9 ± 14.1 |
| 48 | 69.8 ± 24.0 | 17.6 ± 0.9 |
| 72 | 32.2 ± 4.0 | 14.9 ± 3.0 |
| 144 | 3.2 ± 0.8 | 3.5 ± 0.4 |

TABLE 3

Effect of coprine and disulfiram on the yield of $^{14}$C-octopamine ($^{14}$C-OA) formed from $^{14}$C-tyramine ($^{14}$C-TA) in the rat heart: Time course after 150 mg/kg. The experiment is identical with that presented in table 1. Shown are the menas ± s.e.m. (ln ng/g tissue) of in general 3 experiments. Control values are 23.2 ± 2.4 and 3.7 ± 1.1 for $^{14}$C-OA and $^{14}$C-TA, respectively.

| Time | Coprine | | Disulfiram | |
|---|---|---|---|---|
| h | $^{14}C_{-OA}$ | $^{14}C_{-TA}$ | $^{14}C_{-OA}$ | $^{14}C_{-TA}$ |
| 1 | 15.2 ± 5.9 | 2.5 ± 1.2 | 1.5 ± 0.9 | 9.7 ± 0.5 |
| 2 | 20.8 ± 2.0 | 6.1 ± 0.5 | 1.1 ± 0.2 | 15.7 ± 4.2 |
| 4 | 24.4 ± 2.4 | 4.7 ± 0.8 | 2.2 ± 0.4 | 14.5 ± 5.4 |
| 6 | 20.4 ± 4.0 | 5.4 ± 1.3 | 3.2 ± 1.4 | 20.5 ± 4.9 |
| 18 | 11.6 ± 3.6 | 6.3 ± 1.0 | 11.4 ± 4.4 | 9.4 ± 3.2 |
| 24 | 17.5 ± 5.2 | 7.9 ± 1.2 | 11.4 ± 0.7 | 8.5 ± 3.2 |
| 48 | 14.5 ± 2.9 | 4.7 ± 0.8 | 11.9 ± 6.0 | 7.0 ± 0.8 |
| 72 | 22.6 ± 4.1 | 5.3 ± 0.3 | 20.7 ± 3.4 | 8.1 ± 1.3 |
| 144 | 18.4 ± 2.6 | 1.5 ± 0.8 | 20.7 ± 1.1 | 2.2 ± 0.2 |

TABLE 4

Acetaldehyde/ethanol × 10$^3$ in rat alveolar air after different doses of coprine or disulfiram at two fixed intervals, 2 h and 18 h, of pretreatment. Ethanol, 2 g/kg, was given 0.5 h before the measurement. The data are the means ± s.e.m. of ln general 4 experiments. Control value based on 8 experiments: 1.9 ± 0.3.

| Drug | Dose mg/kg 3 | 9 | 27 | 81 | 243 |
|---|---|---|---|---|---|
| Coprine, 2 h | 5.1±1.8 | 10.9±2.7 | 27.2≈6.0 | 28.8±4.1 | 51.8±12. |
| Coprine, 18 h | 3.5±0.6 | 19.2±2.7 | 25.6±1.1 | 40.2±4.1 | 62.5±3.8 |
| Disulfiram, 2 h | 1.9±0.3 | 2.7±0.5 | 2.2±0.2 6.1±1.5 | 13.1±1.6 | |
| Disulfiram, 18 h | 2.6±0.5 | 2.8±0.9 | 5.5±0.6 | 16.1±3.4 | 38.9±6.0 |

TABLE 5

Coprine (hu 14C-OA) formed from $^{14}$C-tyramine ($^{14}$C-TA) in the rat heart: Dose-response curves established at 2 and 18 h. The experiment is identical with that presented in table 3. Shown are the means ± s.e.m. (ln ng/g tissue) of ln general 3 experiments. Control values are 23.8 ± 1.0 and 3.5 ± 0.5 for $^{14}$C-OA and $^{14}$C-TA, respectively.

| Time h | Dose mg/kg | Coprine $^{14}$C-OA | $^{14}$C-TA | Disulfiram $^{14}$C-OA | $^{14}$C-TA |
|---|---|---|---|---|---|
| 2 | 3 | 27.0±1.5 | 3.5±0.9 | 12.0±1.4 | 8.7±2.5 |
| | 9 | 20.3±2.7 | 3.3±0.4 | 8.9±1.3 | 8.7±1.6 |
| | 27 | 16.1±1.9 | 4.3±0.6 | 4.8±2.1 | 14.6±3.2 |
| | 81 | 19.1±2.5 | 8.4±2.3 | 2.1±0.4 | 12.0±0.5 |
| | 243 | 19.9±5.2 | 6.4±2.7 | 1.6±0.5 | 12.7±3.4 |
| 18 | 3 | 22.7±0.9 | 4.0±0.9 | 22.6±2.6 | 5.7±1.1 |
| | 9 | 20.8±2.4 | 4.0±0.8 | 20.3±2.0 | 8.1±1.3 |
| | 27 | 22.8±2.9 | 4.9±0.3 | 20.6±2.6 | 8.0±1.6 |
| | 81 | 19.8±3.2 | 5.1±2.1 | 10.1±1.7 | 6.6±1.7 |
| | 243 | 21.2±3.7 | 3.9±1.0 | 8.2±2.0 | 9.9±2.8 |

We claim:
1. A compound of the formula

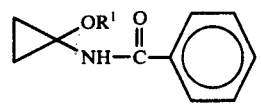

wherein R$^1$ is selected from the group consisting of a hydrogen atom, a methyl group and an ethyl group.

2. A compound according to claim 1 having the formula

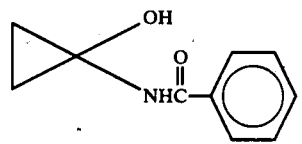

3. A compound according to claim 1 having the formula

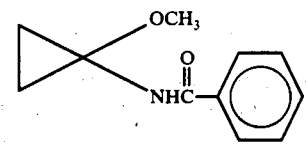

4. A compound according to claim 1 having the formula

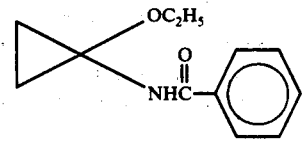

5. A pharmaceutical composition comprising an effective amount of an active ingredient for the treatment of alcoholism of at least one compound of the formula

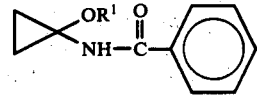

wherein R$^1$ is selected from the group consisting of a hydrogen atom, a methyl group and an ethyl group, and a pharmaceutically acceptable carrier 6. A pharmaceutical composition according to claim 5 wherein the active ingredient is a compound of the formula

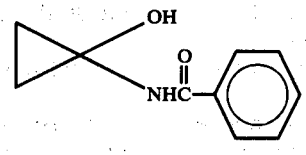

7. A pharmaceutical composition according to claim 5 wherein the active ingredient is a compound of the formula

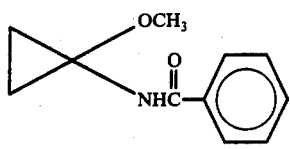

8. A pharmaceutical composition according to claim 5 wherein the active ingredient is a compound of the formula

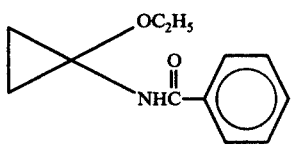

9. A method for the treatment of alcoholism comprising administering to a host suffering from the symptoms of alcoholism a therapeutically effective amount of a compound of the formula

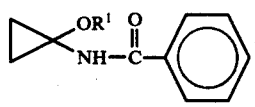

wherein $R^1$ is selected from the group consisting of a hydrogen atom, a methyl group and an ethyl group.

10. A method according to claim 9, wherein the compound administered has the formula

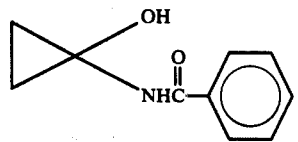

11. A method according to claim 9, wherein the compound administered has the formula

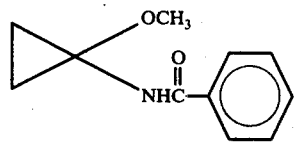

12. A method according to claim 9, wherein the compound administered has the formula

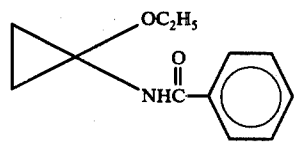

* * * * *

UNITED STATES PATENT OFFICE
CERTIFICATE OF CORRECTION

Page 1 of 3

Patent No. 4,076,840      Dated February 28, 1978

Inventor(s) Per Arvid Emil Carlsson et al.

It is certified that error appears in the above-identified patent and that said Letters Patent are hereby corrected as shown below:

In the Abstract, "$HOOC-(CH_2)_n-CH-CO$" should read
$$\phantom{HOOC-(CH_2)_n-}|\phantom{CO}$$
$$\phantom{HOOC-(CH_2)_n-}NH_2$$

-- $HOOC-(CH_2)_n-CH-CO-$ --;
$$\phantom{HOOC-(CH_2)_n-}|$$
$$\phantom{HOOC-(CH_2)_n-}NH_2$$

Column 1, line 42, after "bad breath" add -- and --;

Column 3, line 47, after "a group" add -- $-H_2^+Cl^-$, $-CO-$, $C_2H_5OCO-$, $CH_3(CH_2)_4CO-$, --;

Column 8, line 24, after "($R_1$=methyl or ethyl" add -- ) --;

Column 9, line 34, after "reaction" add -- of --;

Columns 11 and 12, lines 1-32, the formulas should read:

UNITED STATES PATENT OFFICE
CERTIFICATE OF CORRECTION

Patent No. 4,076,840      Dated February 28, 1978

Inventor(s) Per Arvid Emil Carlsson et al.

It is certified that error appears in the above-identified patent and that said Letters Patent are hereby corrected as shown below:

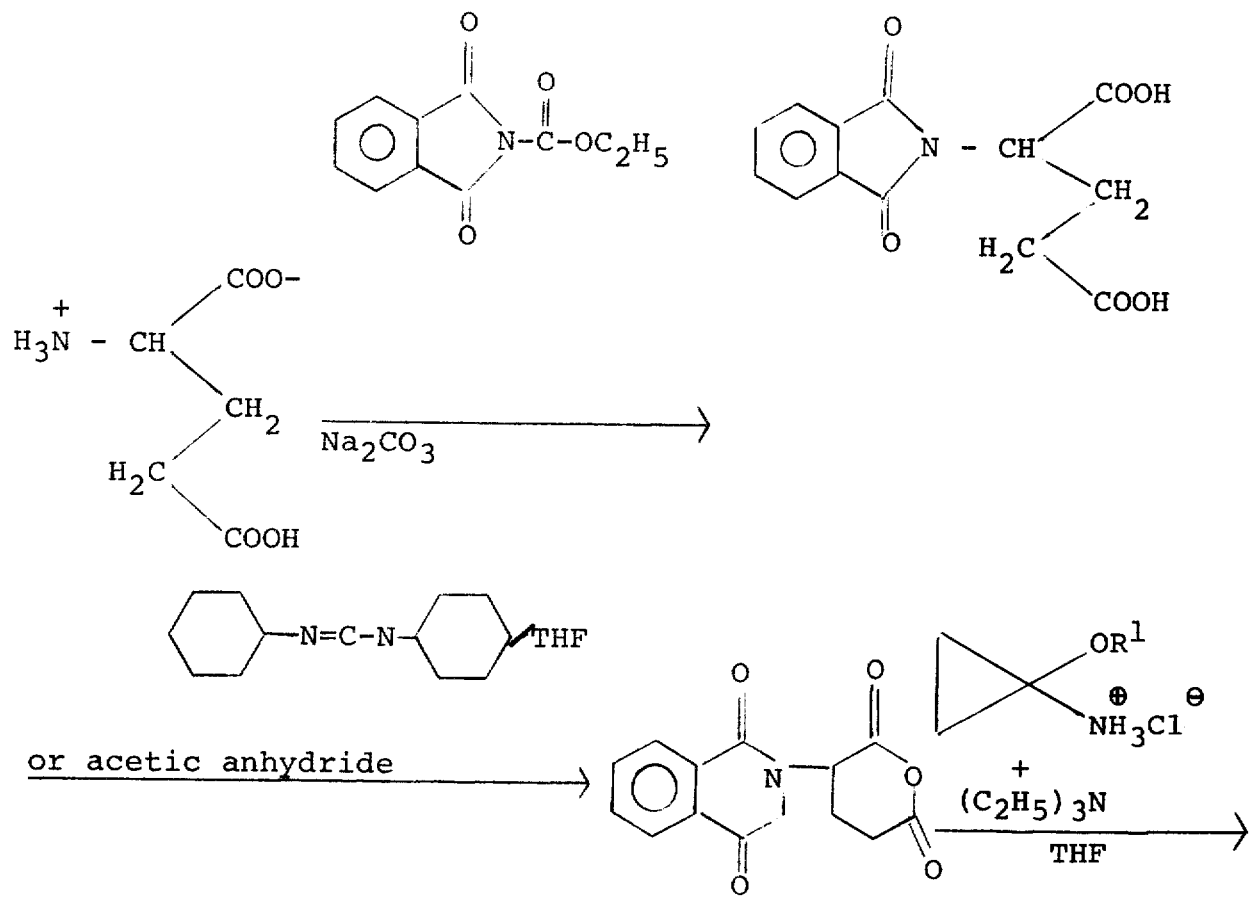

UNITED STATES PATENT OFFICE
CERTIFICATE OF CORRECTION

Patent No. 4,076,840          Dated February 28, 1978

Inventor(s) Per Arvid Emil Carlsson et al.

It is certified that error appears in the above-identified patent and that said Letters Patent are hereby corrected as shown below:

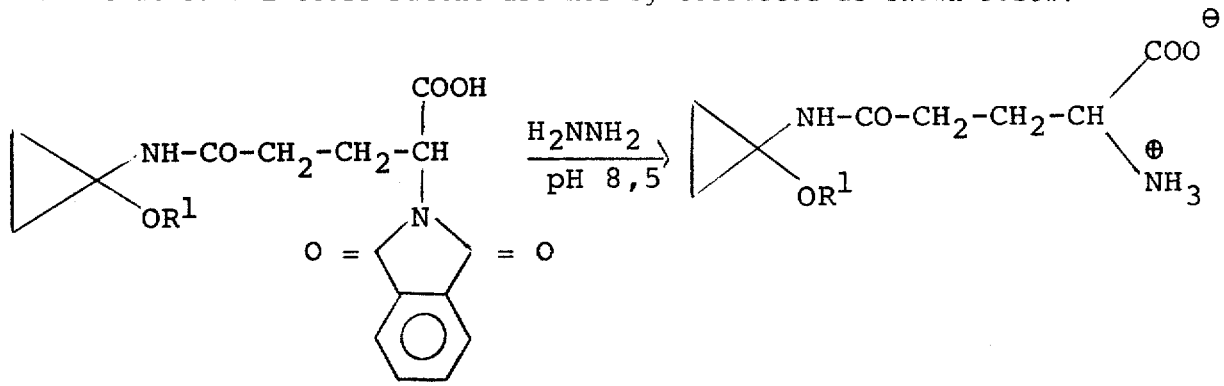

Column 11, lines 61-67, the formulas should read:

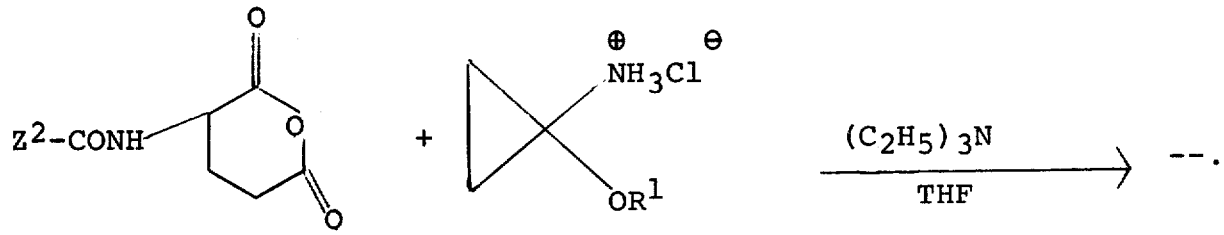

Signed and Sealed this

Twenty-first Day of November 1978

[SEAL]

Attest:

RUTH C. MASON
Attesting Officer

DONALD W. BANNER
Commissioner of Patents and Trademarks